United States Patent [19]

Machiraju

[11] Patent Number: 5,554,184
[45] Date of Patent: Sep. 10, 1996

[54] HEART VALVE

[76] Inventor: Venkat R. Machiraju, 534 Squaw Run E., Pittsburgh, Pa. 15238

[21] Appl. No.: 281,305

[22] Filed: Jul. 27, 1994

[51] Int. Cl.$^6$ ........................................ A61F 2/24
[52] U.S. Cl. ............................ 623/2; 623/901; 606/167
[58] Field of Search ................................ 606/167; 623/2, 623/11, 900, 901

[56] References Cited

U.S. PATENT DOCUMENTS

| | | |
|---|---|---|
| 3,739,402 | 6/1973 | Cooley et al. . |
| 4,261,342 | 4/1981 | Aranguren Duo . |
| 4,490,859 | 1/1985 | Black et al. . |
| 4,629,459 | 12/1986 | Ionescu ........................ 623/2 |
| 4,655,773 | 4/1987 | Grassi . |
| 4,960,424 | 10/1990 | Grooters ....................... 623/2 |
| 5,078,739 | 1/1992 | Martin ......................... 623/2 |
| 5,163,954 | 11/1992 | Curcio et al. . |
| 5,415,667 | 5/1995 | Frater ......................... 623/2 |
| 5,443,501 | 8/1995 | Barmada ....................... 623/2 |

FOREIGN PATENT DOCUMENTS

| | | | |
|---|---|---|---|
| 0402036 | 12/1990 | European Pat. Off. .......... | A61F 2/24 |
| 1710032 | 2/1992 | U.S.S.R. ....................... | A61B 17/00 |
| 1771701 | 10/1992 | U.S.S.R. ....................... | A61B 17/00 |
| 2206395 | 1/1989 | United Kingdom .............. | A61F 2/24 |

*Primary Examiner*—Michael A. Brown
*Attorney, Agent, or Firm*—Webb Ziesenheim Bruening Logsdon Orkin & Hanson, P.C.

[57] ABSTRACT

A heart valve, and a technique for effecting valve replacement or repair, which partially or completely replaces the mitral (or tricuspid) valve with an autologous graft from the pericardium, fascia lata or even the dura mater, or a bovine or porcine pericardial or other synthetic sheet material equivalent thereof, preferably in a configuration which substantially restores the original anatomy of the heart including chordae tendineae attached to adjacent papillary muscles of the heart. Most preferably, a section of the patient's pericardium is cut to a shape including two leaflets, with each leaflet having a trabeculated tier of chordae tendineae terminating in a spear-shaped tab. The two leaflets are cut out as a single unit, and the two far ends are sutured together to yield a bileaflet valve having appended chordae and tabs.

16 Claims, 3 Drawing Sheets

HEART VALVE

FIELD OF THE INVENTION

The present invention relates to surgical techniques for correcting diseases of the mitral or tricuspid valve, as well as a replacement mitral valve or tricuspid valve structure, which improve upon the valves and techniques of the prior art.

BACKGROUND OF THE INVENTION

Natural heart valves are thin membranes which can seem to the uninitiated to be too fragile to open and close constantly hour after hour to keep a human heart pumping for a lifetime. Despite their apparent fragility, however, human heart valves are generally tough and reliable. Surgeons who repair or replace heart valves thus face a daunting challenge: to reproduce the performance and longevity of natural heart valves using tissue or synthetic materials and surgical techniques. Not surprisingly, many if not all prior art valve replacement and repair techniques have been acknowledged as only partially meeting this challenge, inasmuch as they provide only a temporary correction (10-20 years or so, and sometimes significantly less) and do not reproduce the original valve's function or efficiency.

As if the above challenges in heart valve technology were not enough, existing techniques and prostheses are also plagued by enormous costs. Understandably, synthetic structures and xenografts must be carefully engineered to create not only generally biocompatible structures but nonimmunogenic ones as well. Even seemingly safe materials such as surgical titanium and stainless steel, and polymers such as polyether polyurethane, have demonstrated troublesome biocompatibility or immunogenicity problems, and the useful life of a prosthesis incorporating them is thus unfortunately shortened. Alternative, expensive materials have been developed but even these synthetic materials and treated xenografts are imperfect.

Finally, one heart valve in particular—the mitral valve—has traditionally been less satisfactorily replaced than the other valves of the heart. (The same might be said of the mitral and tricuspid valves both, except that as a practical matter tricuspid valve replacement is not as important as mitral valve replacement—one tricuspid valve is replaced for every 1,000 mitral valves, in large part because repair can under certain circumstances succeed with annuloplasty alone.) The traditional difficulties in replacing or repairing mitral valves are due primarily to the challenge inherent in reproducing the natural valve structure including the chordae tendineae. The chordae tendineae connect the valve leaflets to the papillary muscles of the heart. Surgical replacement of the chordae tendineae in conjunction with mitral valve repair has previously been attempted, but with limited success. The area available for suturing one of the chordae directly to a papillary muscle is very small, due to the narrow width of a chord, and attempted attachment has invariably caused either the suture and/or the chord to pull free of the papillary muscle within a short time after surgery. Mitral valve replacement without reconstruction including chordae tendineae does not restore the original structure of the heart. It is helpful to note that standard trileaflet prosthetic valves for aortic or pulmonary valve replacement are not anatomically deficient with respect to their intended loci. Those same standard valves, however, cannot replace the mitral valve without anatomic compromise. A need therefore remains for a mitral (tricuspid) heart valve which can claim the same distinction.

Accordingly, a new mitral valve, and a method for replacing or repairing the mitral valve, are needed in the cardiac surgery arts. An especial need persists for a mitral valve which is biocompatible and thoroughly nonimmunogenic, can be made and surgically implanted at substantially reduced cost (in comparison to prior art mitral valves), and which accurately reproduces and restores the original anatomy of the heart including chordae tendineae. Additionally, the mitral valve should be suitable for use in the tricuspid position, in those instances in which tricuspid valve replacement is indicated.

SUMMARY OF THE INVENTION

In order to meet these needs, the present invention is a heart valve, and a technique for effecting valve replacement or repair, which partially or completely replaces the mitral (or tricuspid) valve with an autologous graft from the pericardium, fascia lata or even the dura mater, or a synthetic sheet material equivalent thereof, preferably in a configuration which substantially restores the original anatomy of the heart including chordae tendineae attached to adjacent papillary muscles of the heart. Most preferably, a section of the patient's pericardium is cut to a shape including two leaflets, with each leaflet having a trabeculated tier of chordae tendineae terminating in a spear-shaped tab. The two leaflets are cut out as a single unit, and the two far ends are sutured together to yield a bileaflet valve having appended chordae and tabs. Prior to surgical implantation, the pericardial tissue is cured in an aqueous glutaraldehyde solution. The invention also embraces variations on this preferred embodiment including, but not limited to, the use of the above-identified substitute tissues other than pericardium as well as synthetic materials under certain circumstances, a reduced number of chordae and the use of alternative curing (or crosslinking) solutions.

DETAILED DESCRIPTION OF THE INVENTION

Figure 1:
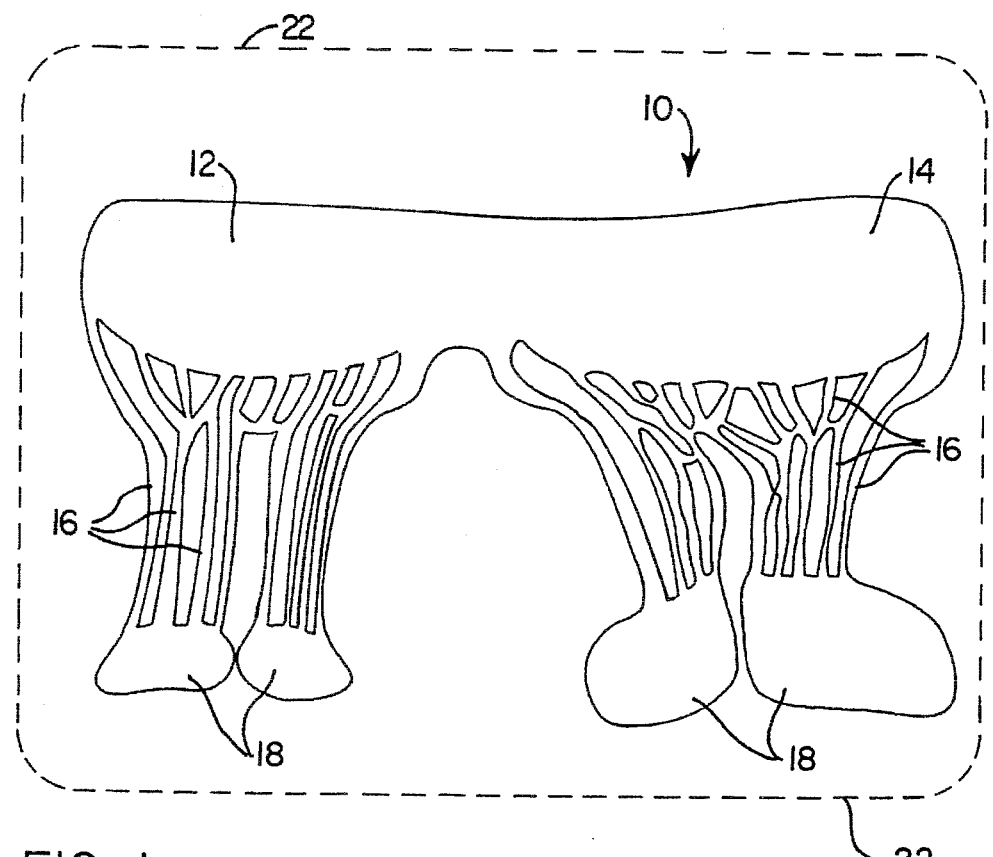
FIG. 1 is a plan view of an excised and shaped pericardium according to the preferred embodiment of the present invention.

The present invention is a heart valve, and a technique for effecting heart valve replacement or repair, which partially or completely replaces the mitral (or tricuspid) valve with an autologous graft from the pericardium, fascia lata or even the dura mater, or an equivalent bovine or porcine or other pericardial or synthetic sheet material. The autologous graft material is preferably precut and shaped into a configuration which substantially restores the original anatomy of the heart, including the chordae tendineae attached to adjacent papillary muscles of the heart. Most preferably, a section of the patient's pericardium is cut to a shape including two leaflets, with each leaflet having a trabeculated tier of chordae tendineae terminating in a spear-shaped tab. The two leaflets are cut out as a single unit, and then the two far ends are sutured together to yield a bileaflet valve having appended chordae and tabs. Prior to surgical implantation, and either before or after precutting and shaping, the pericardium graft is preferably cured in an aqueous glutaraldehyde solution. Apart from its preferred embodiment, the invention also embraces variations on this preferred embodiment including, but not limited to, the use of the dura mater or fascia lata instead of the pericardium as well as bovine or porcine pericardial or other synthetic materials under certain circumstances, a reduced number of chordae and alternative curing (or crosslinking) solutions. The synthetic materials can include any of the synthetic polymers accepted for use in cardiac repair and valve replacement, and recent developments in this field have yielded excellent sheet materials which will substitute for the pericardium or other tissue when autologous tissue is unavailable for some reason. It should be borne in mind, however, that the use of the patient's own pericardial or other tissue is essential to the preferred embodiment of this invention.

The pericardium is the protective sheath around the heart, and although ligaments anchor it and therefore also the heart itself within the chest cavity, it is not a structure necessary for good health or heart function. In other words, despite the protective and anchoring effect of the intact pericardium, the pericardium may be completely excised without any detriment to the patient. An important aspect of the preferred embodiment of the present invention, therefore, is the use of the patient's own pericardial tissue to construct a prosthetic mitral valve. The use of the patient's own tissue in a tissue heart valve greatly minimizes if not eliminates any biocompatibility, immunogenicity or general rejection problems which nonautologous materials may cause.

Although the untreated pericardium may be used to construct the present mitral valve, preferably the pericardial tissue is treated to cure or crosslink it, to stabilize it and to increase tensile strength with commensurate decrease in its elongation under load. Most preferably, the pericardium is cured in sterile 0.1–0.8% aqueous glutaraldehyde, although comparable crosslinking or curing agents may be determined without undue experimentation because they need merely stabilize the existing tissue without altering its antigenicity (or lack thereof). The crosslinking or curing agent should itself be histocompatible or, in other words, any residue of the curing or crosslinking agent should not be cytotoxic or otherwise undesirable. An example of a crosslinking agent which is not acceptable is formaldehyde, which is both cytotoxic and carcinogenic.

In the context of discussing the pericardium, it should also be noted that pericardial tissue is a sheet material which is different on its two sides. Lining the interior of the pericardial sac is a thin, moist membrane; the outside surface of the pericardium is dry and relatively rougher. The significance of this difference will become apparent later in the description of the invention.

In the most preferred embodiment of the invention, a human patient's own pericardium is used to create a heart valve graft when replacement of the mitral or tricuspid valves is indicated. The pericardium is surgically incised, cut to shape and sutured into a ring (alternatively the pericardium may be sutured into a tube and then cut to shape), stabilized in a crosslinking or curing agent, usually liquid, and surgically implanted into the mitral or tricuspid valve locus in the heart. Alternatively, the pericardial tissue may be stabilized first, then cut to shape and sutured. In fact, after the pericardium is excised, cutting, stabilizing (crosslinking) and suturing may take place in any order, although after the pericardium is stabilized it must be thoroughly rinsed. A typical protocol would include stabilizing the pericardial tissue for ten minutes in the glutaraldehyde solution, followed by a five-minute rinse with running sterile water, but this protocol is exemplary only. It is within the skill of the art to stabilize (crosslink) and to rinse human tissue.

An important aspect of the invention is the shape into which the pericardial tissue is cut. FIG. 1 illustrates the shape of the cut pericardium according to the preferred embodiment of the present invention. The cut pericardium forms a heart valve 10 having an anterior leaflet 12, a posterior leaflet 14, a plurality of chordae tendineae 16 and papillary muscle graft tabs 18. The chordae tendineae 16 are trabeculated or, in other words, cascade in a tier from the leaflets 12, 14 to the papillary muscle graft tabs 18. In other words, the chordae tendineae 16 are most numerous where they directly append the leaflets 12, 14, but between the leaflets 12, 14 and the papillary muscle graft tabs 18 they converge, thus reducing the number of chordae 16 appended to the tabs 18. The preferred embodiment of the invention includes about twenty chordae tendineae 16 directly appending the leaflets 12, 14, with those twenty chordae converging into about sixteen chordae at the interface between the chordae and the papillary muscle graft tabs. Incidentally, the study of normal heart anatomy reveals that about twenty chordae tendineae append the mitral valve leaflets, and thus the preferred embodiment recreates this normal anatomical feature of the heart.

Figure 4:
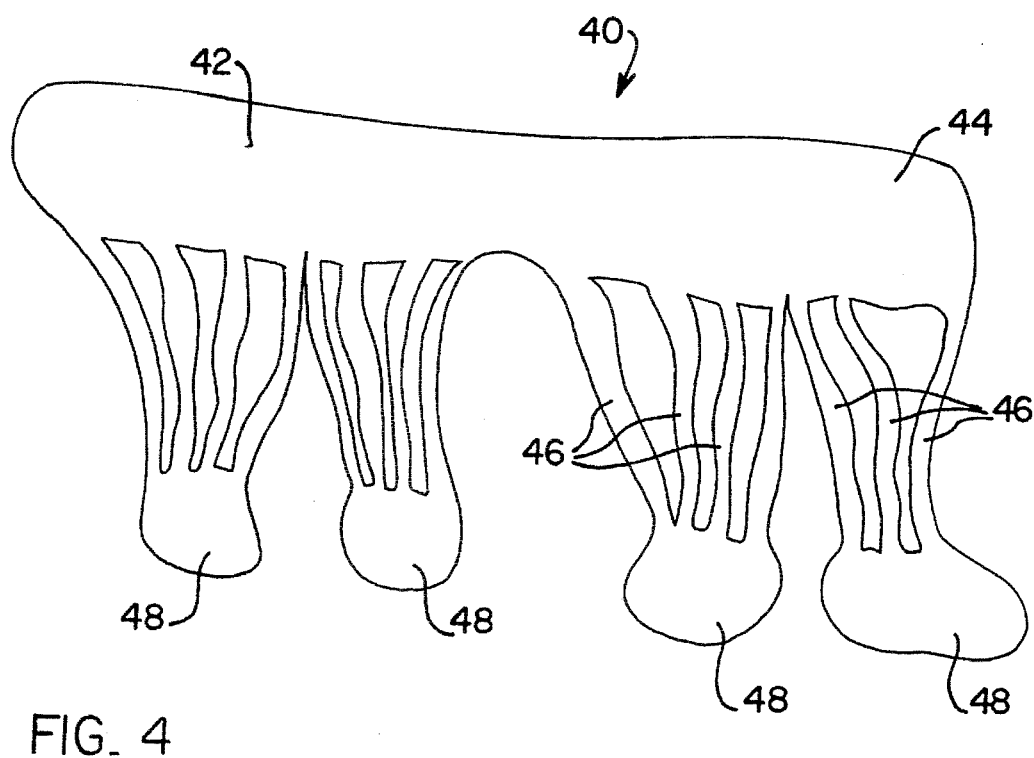
FIG. 4 is a plan view of a heart valve according to an alternative embodiment of the invention.

As an alternative to the preferred embodiment, the cut pericardial tissue may incorporate fewer chordae 16, and with reduced or eliminated trabeculation, than described above and still remain within the scope of the present invention. FIG. 4 shows a pericardium cut in accordance with an alternate embodiment of the invention, to yield a heart valve 40 in which fifteen chordae tendineae 46 which append the leaflets 42, 44 connect directly to the papillary muscle graft tabs 48, without converging.

Figure 2:
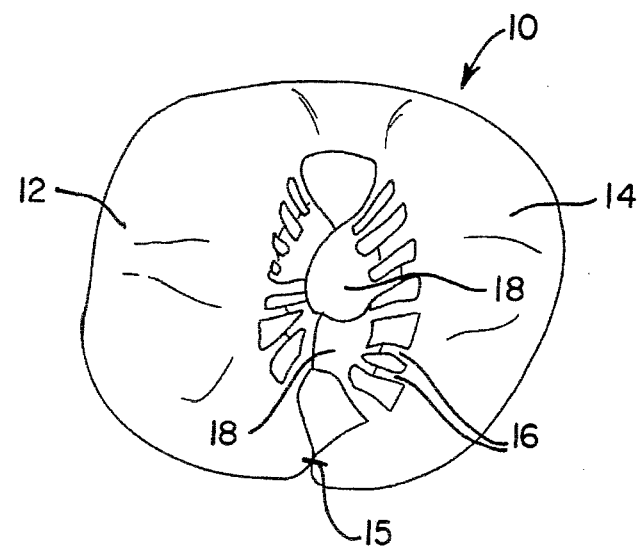
FIG. 2 is a plan view of the pericardium of FIG. 1 after the two leaflets are sutured into an annulus which is then laid flat, with the chordae in the center.

Referring now to FIG. 2, the heart valve 10 of FIG. 1 is shown in its annular and flattened orientation, after the anterior and posterior leaflets 12, 14 are sutured together with a suture 15. More than one suture may be used, but a single suture 15 is shown in FIG. 2 for clarity. The sheet is shown flat, with the chordae tendineae 16 and the papillary muscle graft tabs 18 literally piled in the center of the circular leaflets 12, 14. When the heart valve 10 is sutured into place within the patient's heart, attachment of the leaflets 12, 14 in the actual valve location plus suturing of the papillary muscle graft tabs 18 to the adjacent papillary muscles, the configuration shown in FIG. 2 is lost and the heart valve 10 takes on the configuration shown in FIG. 3.

Figure 3:
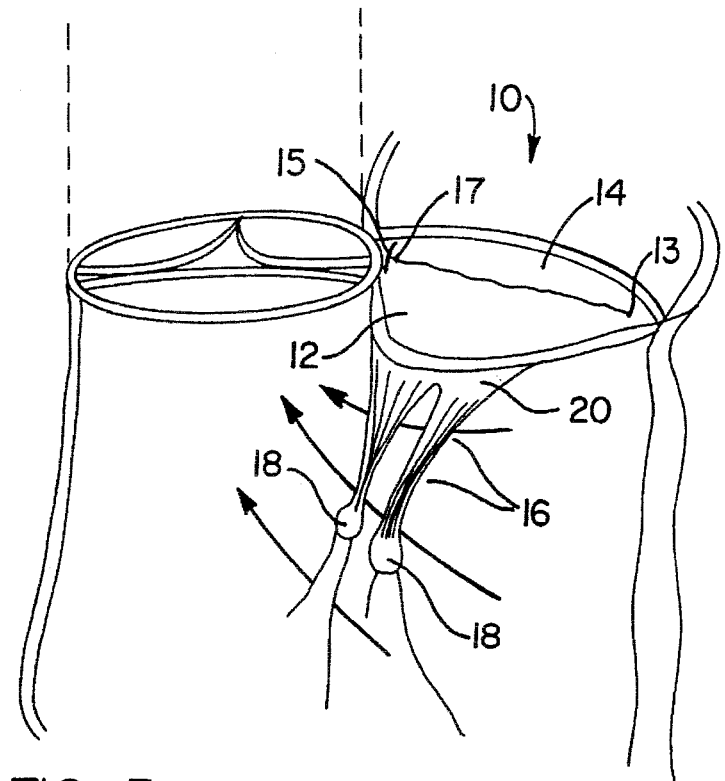
FIG. 3 is a section of the left ventricle of the heart, showing the heart valve of FIGS. 1 and 2 in place within the heart at the mitral valve position, and also showing its position relative to the aortic valve as well as the importance of preserving the cardiac anatomy with respect to the chordae tendineae and (pumping) blood flow therethrough.

FIG. 3 is a partial section of the human left atrium and ventricle, just anterior of the anterior leaflet of the mitral valve, showing the present heart valve in place in a human heart in the mitral position. The same structures as are visible in FIG. 1 may be seen in FIG. 3. The anterior leaflet 12 and posterior leaflet 14 join at the anterior commissure 17, opposite the posterior commissure 13, and the papillary muscle graft tabs 18 are visibly grafted onto their respective papillary muscles. The suture 15 of the present heart valve preferably coincides with the anterior commissure 17, because this locus is relatively immobile within the heart, compared to the posterior commissure 13, and thus exerts minimal stress on the suture 15. Solid arrows show blood flow through the left ventricle and also illustrate the importance of the spaces between chordae tendineae—blood flows all through and around them during the pumping of the heart.

With continued reference to FIG. 3, the sheet material taken from the pericardium has definite preferred right and wrong sides or, more specifically, has a side which should face the atrium and a side which should face the ventricle when the valve is closed. The side of the pericardium which bears the thin, moist membranous lining should face the atrium, and the dry, relatively rougher side 20 should face the ventricle for the purposes of the preferred embodiment of the invention. The reason is as follows. Blood flow from the atrium to the ventricle is largely passive flow, whereas blood flow through the ventricle is vigorous as a result of heart muscle pumping. In the unlikely event that any blood clots might form anywhere on the present mitral valve, they would theoretically tend to do so on the atrial side of the valve, where the relatively passive blood flow might permit it. However, on the ventricular side of the valve the strong blood flows minimize or eliminate any possibility of clot formation even on the dry and relatively rougher side 20 of the pericardial tissue. Thus, having the moist membrane of the pericardium face the atrium constitutes the preferred orientation, although it should be recognized that the present invention embraces the grafting of the shaped pericardium in the mitral or tricuspid valve positions in either of the two possible orientations.

If desired, a standard suture cuff may be used to reinforce the leaflets as the present valve is sutured into place. Alternatively, only the suture 15 need be reinforced with a small Dacron graft. The suture cuff would ordinarily be placed at the suture line of the leaflets on the moist membranous side of the pericardium. Other portions of the present mitral valve may conceivably be reinforced for suturing also, in the same way. In particular, thin strips of Gore-Tex polymer may be sutured alongside the chordae, to strengthen them. Generally, however, the heart valve of FIGS. 1 or 4, or other heart valves according to the present invention, may be sutured into place during routine cardiac surgery by suturing the respective anatomical portions into their proper place. The upper edges of the anterior and posterior leaflets 12, 14 (in other words, the edges opposite the chordae) may be trimmed by the surgeon at the time of suturing, for an exact fit. Ordinarily this trimming is done after the leaflets have been sutured into place.

As a general rule, the mitral valve has a diameter of about 28–40 mm, after the leaflets are sutured together as shown in FIG. 2. Different hearts have different sizes and commensurately differing valve sizes, but when valves throughout this range can be prepared it is virtually certain that one of the sizes will fit any given human patient. As a practical matter, it is best to have a choice of three sizes accommodating the small valve (28–30 mm diameter) the medium valve (32–34 mm) and the large valve (36–38 mm).

Figure 5:
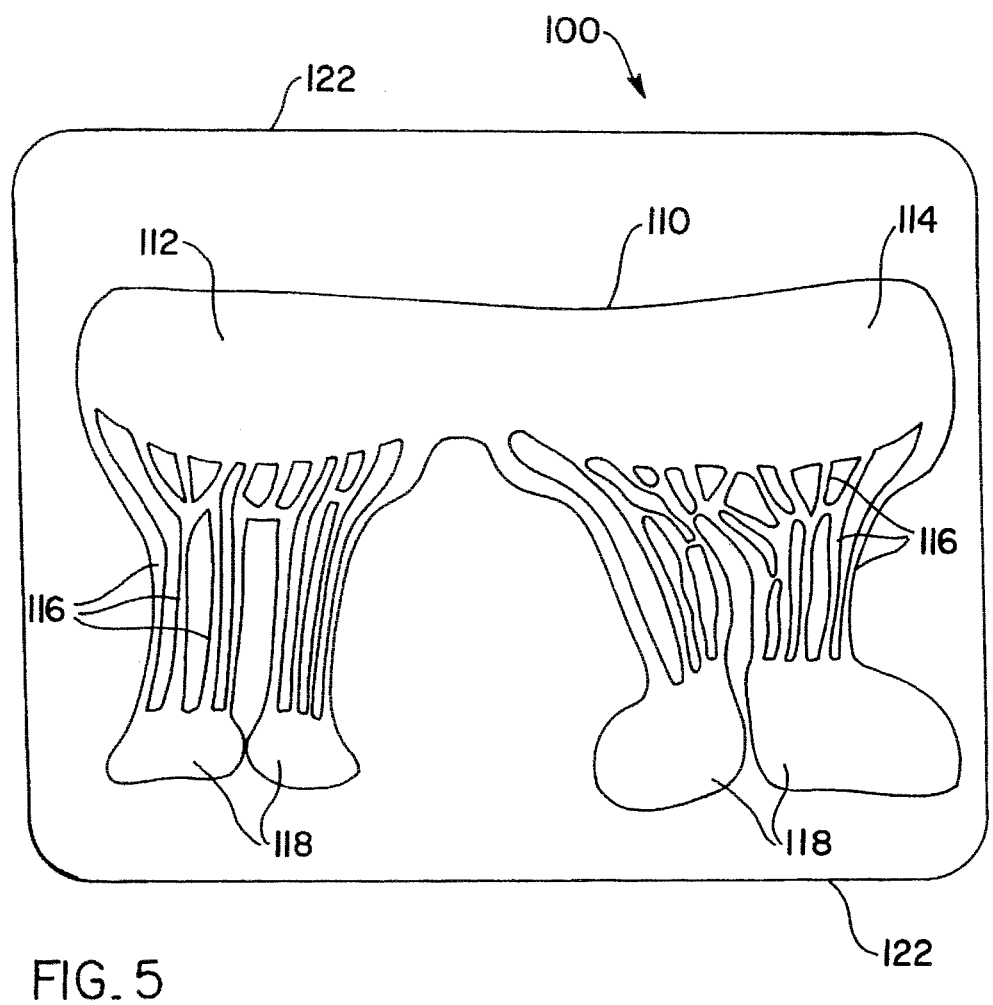
FIG. 5 is a plan view of a cutting tool according to the present invention.

In order to ensure availability of the above described range of sizes, as well as to assure rapid availability of a shaped, excised pericardium from the same surgical procedure, a preferred tool for implementing the present invention is a tool for cutting or stamping the pericardial sheet. Such a tool may be represented by FIG. 1 if the dotted line 22 represents the tool circumference, the solid lines represent the cutting blades and the view is sectional through the blades with the tool backing in the foreground. FIG. 5 discloses such a tool 100, having a tool backing 122 bearing a blade 110 thereon, with each of the same heart valve shapes being defined by the shape of the blades as are shown in FIG. 1, namely, the anterior leaflet 112, the posterior leaflet 114, the chordae 116 and the papillary muscle graft tabs 118. Such a tool may be incorporated into a stamping machine so that an excised pericardium may be quickly and accurately cut to the necessary shape. Preferably, the tool has disposable blades or is disposable in entirety. If only the blades are disposable, then the tool itself must be autoclavable. The invention also embraces the use of a template for cutting the valve shown in FIG. 1, although because the pericardium is tough and strong a cutting tool for machine assisted stamp cutting is preferable to a template for manual cutting. Even so, manual or power or laser cutting of the pericardium are all contemplated for possible use in the practice of the invention.

Additional chemical treatments of the present heart valve may be conducted without departure from the scope of the present invention. Anticalcification agents, in particular, may be contacted onto all or a portion of the valve to assure minimization or elimination of unwanted in vivo calcification of the valve. Aminooleic acid is a possible anticalcification agent; others are identified on an ongoing basis.

Although the invention has been described with particularity above, with respect to particular methods and materials, the invention is only to be limited insofar as is set forth in the accompanying claims.

I claim:

1. A method for repairing a human heart valve, comprising the steps of cutting a single sheet of a natural or artificial sheet material into the shape of an excised human heart valve including at least one trabeculated tier of chordae tendineae, said tier terminating in a papillary muscle graft tab, and surgically implanting the cut sheet material into the heart of a patient in whom heart valve repair is indicated.

2. The method according to claim 1 wherein said step of cutting a natural or artificial sheet material is conducted with a cutting tool having blades configured in the shape of an excised human heart valve.

3. The method according to claim 1 wherein said step of cutting a natural or artificial sheet material is conducted with a cutting tool having blades configured in the shape of an excised human mitral valve.

4. The method according to claim 3 wherein said sheet material is selected from the group consisting of autologous pericardium, autologous fascia lata, autologous dura mater, bovine pericardium, porcine pericardium and biocompatible polymer.

5. The method according to claim 4 wherein said sheet material is autologous pericardium.

6. The method according to claim 3 wherein said shape of an excised human mitral valve further comprises an anterior leaflet connected to a posterior leaflet, a plurality of papillary muscle graft tabs and a plurality of chordae tendineae connecting said leaflets to said papillary muscle graft tabs.

7. The method according to claim 3 wherein said shape of an excised human mitral valve includes about 20 chordae tendineae.

8. A cutting tool for preparing a human heart valve graft, comprising a backing and at least one blade configured in the shape of an excised human heart valve including at least one trabeculated tier of chordae tendineae, wherein said chordae tendineae have papillary muscle graft tabs appended thereto.

9. A cutting tool according to claim 8 wherein said at least one blade is disposable, said backing is autoclavable, and said tool is adapted for inclusion in a mechanical cutting system.

10. A cutting tool for preparing a human heart valve graft, comprising a substrate bearing cutouts defining the shape of an excised human mitral valve including chordae tendineae.

11. A method for repairing a human mitral valve, comprising the steps of:

excising at least a portion of the pericardium, in a single piece, of a patient in whom mitral valve repair is indicated;

cutting said pericardium into the shape of a human mitral valve including at least one trabeculated tier of chordae tendineae terminating in a papillary muscle graft tab;

curing the pericardium thus cut in a crosslinking solution, followed by rinsing; and surgically implanting the cut and cured pericardium in the heart of a patient in whom mitral valve replacement is indicated.

12. The method according to claim 11 wherein said step of cutting said pericardium is conducted with a cutting tool having blades configured in the shape of an excised human mitral valve including chordae tendineae.

13. The method according to claim 11 wherein said shape of an excised human mitral valve including chordae tendineae further comprises an anterior leaflet connected to a posterior leaflet, a plurality of papillary muscle graft tabs and a plurality of chordae tendineae connecting said leaflets to said papillary muscle graft tabs.

14. The method according to claim 13 wherein said shape of an excised human mitral valve further includes about 20 chordae tendineae.

15. The method according to claim 14 wherein said chordae tendineae are trabeculated.

16. The method according to claim 14 wherein said crosslinking solution is aqueous glutaraldehyde.

* * * * *